United States Patent
Holmes et al.

(10) Patent No.: US 10,119,894 B2
(45) Date of Patent: Nov. 6, 2018

(54) SYSTEM AND METHOD FOR DETECTING OVERLOADING, WEAR AND/OR FAILURE OF A BALL JOINT

(71) Applicant: ZF Friedrichshafen AG, Friedrichshafen (DE)

(72) Inventors: Eric Holmes, Ann Arbor, MI (US); Timothy LaBuda, Hazel Park, MI (US); Joel Lautermilch, South Lyon, MI (US)

(73) Assignee: ZF Friedrichshafen AG, Friedrichshafen (DE)

( * ) Notice: Subject to any disclaimer, the term of this patent is extended or adjusted under 35 U.S.C. 154(b) by 160 days.

(21) Appl. No.: 15/053,090

(22) Filed: Feb. 25, 2016

(65) Prior Publication Data

US 2017/0248505 A1    Aug. 31, 2017

(51) Int. Cl.
*G01N 3/56* (2006.01)
*F16C 11/06* (2006.01)
*F16C 41/00* (2006.01)

(52) U.S. Cl.
CPC ............. *G01N 3/56* (2013.01); *F16C 11/0628* (2013.01); *F16C 11/0647* (2013.01); *F16C 41/008* (2013.01)

(58) Field of Classification Search
CPC ........ G01N 3/56; G01N 27/20; G01N 27/205; G01N 27/24; G01B 7/144; F16C 11/0628; F16C 11/0647; F16C 17/246; Y10T 403/20
See application file for complete search history.

(56) References Cited

U.S. PATENT DOCUMENTS

| | | | | |
|---|---|---|---|---|
| 4,626,121 A * | 12/1986 | Tajima | ................... | F16C 11/086 116/208 |
| 4,679,957 A * | 7/1987 | Bauer | ...................... | F16C 11/06 403/115 |
| 6,206,573 B1 * | 3/2001 | Miller | ................... | F16C 17/246 384/448 |
| 7,048,461 B2 * | 5/2006 | Williams | ............ | F16C 11/0642 403/135 |
| 7,367,742 B2 * | 5/2008 | Brunneke | ........... | F16C 11/0647 403/122 |
| 7,695,212 B2 * | 4/2010 | Spratte | ................... | B60G 7/005 324/207.25 |
| 7,762,736 B2 * | 7/2010 | Ersoy | ....................... | B60D 1/30 403/122 |

(Continued)

FOREIGN PATENT DOCUMENTS

DE    102008041050 A1    2/2010

*Primary Examiner* — Natalie Huls
(74) *Attorney, Agent, or Firm* — Davis & Bujold PLLC; Michael J. Bujold (57) ABSTRACT

A system and method for detecting wear and/or failure of a ball joint. The system having a ball housing which retains a ball head of the ball joint therein. A ball race is received within the ball housing and receives the ball head of the ball joint. An inwardly facing surface of the ball race engages the ball head such that the ball head can pivot in relation to the ball housing. A detection component is supported by the ball race and is spaced from an exterior surface of the ball head by a set distance. The detection component issues an indicator signal to alert a driver when the detection component detects at least one of a worn or a failure condition of the ball joint.

10 Claims, 5 Drawing Sheets

(56) References Cited

U.S. PATENT DOCUMENTS

| | | | |
|---|---|---|---|
| 2003/0070476 A1* | 4/2003 | Heidemann | F16C 11/0647 73/117.02 |
| 2004/0067096 A1* | 4/2004 | Ersoy | B60G 7/005 403/137 |
| 2005/0207830 A1* | 9/2005 | Brunneke | F16C 11/0647 403/122 |
| 2006/0029461 A1* | 2/2006 | Benick | F16C 11/0647 403/122 |
| 2008/0199247 A1* | 8/2008 | Spratte | F16C 11/0647 403/27 |
| 2009/0087253 A1* | 4/2009 | Spratte | B60G 17/019 403/131 |
| 2015/0176638 A1* | 6/2015 | Hebrard | F16C 11/0647 324/682 |

* cited by examiner

SYSTEM AND METHOD FOR DETECTING OVERLOADING, WEAR AND/OR FAILURE OF A BALL JOINT

FIELD OF THE INVENTION

The present invention relates to a system and method of detecting the overloading, wear and/or failure of a ball joint.

BACKGROUND OF THE INVENTION

Ball joints have been used in automotive vehicles for long periods of time and are commonly associated with vehicle suspension and steering systems. They are used to couple two or more elements together, for example wheel hubs are generally coupled to the rest of the suspension by way of a ball joint while at the same time enabling movement of these elements with respect to each other in a number of directions. Ball joints basically include a metal ball that is supported within a cage or socket. Typically the space between the ball and the socket is filled with grease so as to reduce wear and it is common to place a rubber seal over the ball joint to help keep water and dirt out. Occasionally rubber seals fail and as a result, water, dirt and/or other impurities may enter into the ball joint, and grease may also leak out of the ball joint which in turn reduces the usable life of the ball joint. Ball joints can also fail as a result of impact forces such as when the wheel strikes a pot hole or curb for example. Corrosion, wear, damage and/or failure of ball joints is often manifest audibly and/or tacitly. Indications that a typical ball joint may be failing include clicking, popping or snapping noises. These noises may develop into a squeaking sound when driving the vehicle, during acceleration and/or also when hitting bumps. Another indication of ball joint failure may be 'thud' noises that come from the suspension when going over bumps. Ball joints in which the grease or other lubricant has leaked can be recognized by a dramatic increase of friction causing the steering to stick or become difficult.

The results of ball joint failure can be dangerous since the angle of the wheel becomes unconstrained, thus causing loss of control of the automobile. The lack of control of the steering angle of a tire can cause damage to the tire as well as other parts of the vehicle.

Over the past 10 years many improvements have been made in ride technology with advances in electronic and smart systems. Although these systems enhance the operation of automobiles, they also tend to reduce the audible and tactile effects caused, for example, by corrosion, wear, damage and/or failure of ball joints and thus make it much more difficult to detect worn or damaged ball joints. It is possible that a driver may not even notice that a ball joint has been damaged and thus will continue driving the automobile in this state.

A method is known from DE 10 2008 041 050 A1 for measuring the wear of a ball and socket joint. For this purpose, a magnetic field parameter is measured with a magnetic field sensor at a point of time, in which either a force or no force is acting on a ball stud of a ball joint. The measured magnetic field parameter is then transmitted from the magnetic field sensor to a control unit for evaluation. By evaluating the measured sensor signal, the wear condition of the ball and socket joint can be determined. Specifically, the ball and socket joint includes a ball stud having a ball that is pivotally and rotatably supported by a ball socket. The ball and socket joint includes an angle measuring device having a magnet that is fixed to one of the ball and the ball socket, and a magnetic field sensor that is fixed to the other of the ball and the ball socket. The magnetic field sensor measures the intensity of the magnetic field generated by the magnet in at least one spatial direction at a first time point when the ball and socket joint is under a first load. The magnetic field sensor then measures the intensity of the magnetic field generated by the magnet in the same spatial direction at a second time point when the ball and socket joint is under a second load. As the position of the ball relative to the ball socket depends on the loads acting on the ball and socket joint, the magnetic field intensity measurements are then evaluated with reference to the loads placed the ball and socket joint to determine the wear condition of the ball and socket joint. Although this ball and socket joint may be beneficial for its intended purpose, the sensor merely detects the position of the ball with respect to the socket as the magnet moves in relation to the sensor and does not determine wear or failure of the ball joint.

SUMMARY OF THE INVENTION

It is therefore an objective of the invention to provide a system and method for detecting overloading, wear and/or failure of a ball joint. The system that detects the ingress of water, corrosion, wear, damage, failure and/or overload of ball joints and informing driver that the ball joint is suspect and the automobile should be serviced. In also an objective of the invention to detect the ingress of moisture into the ball joint and notify the driver such that corrective action, e.g., replacement of the part through service, may be taken before the moisture causes corrosion and wear of the ball joint.

Another objective of the present invention is to provide a ball joint having a system for detecting overloading, wear and/or failure of a ball joint. The ball joint includes a ball stud having a ball head that is received within a ball race which is in turn received within a joint housing. The ball race has an exterior surface that mates with the inwardly facing surface of the joint housing and an inwardly facing surface that conforms to substantially the same shape as the ball head. The ball head is held in position within the joint housing by the ball race such that the center point of the ball is generally fixed in position within the joint housing and can rotate about its rotational axis and can laterally pivot with respect to the ball housing.

Yet another objective of the present invention is to provide a system and method for detecting overload, wear and/or failure of a ball joint comprising a ball race having a body formed of a first material. A framework of ribs, tines, branches and/or prongs that are made of a second material is encased within or attached to body of the ball race. The second material is generally harder than the first material forming the body and intended to make a noise when in contact with the ball head. Due to the difference in hardness between the first and the second materials, the ball race becomes deformed when a sufficient force is placed on the ball joint such as when the vehicle hits a pot hole or curb. This deformation of the framework causes an uneven distribution of contact between the ball race and the ball head. Contact between the ball head and the deformed ball race harder material results in loud noises during continued movement of the automobile which in turn signals the driver that the ball joint may have failed and that service of the automobile is required.

A further objective of the present invention is to provide a system and method for detecting overload, wear and/or failure of a ball joint having a sensor module which detects these conditions of the ball joint and alerts the driver of the same. In a variation of the inventive system for detecting overload, wear or failure of a ball joint, the ball is preferably electrically conductive and the ball race is electrically nonconductive. The body of the ball race includes an electrical circuit that is encased within the nonconductive material of the body. The electrical circuit can be formed, for example, by a printed circuit or electrical leads that extend through the body as ribs, tines, branches and/or prongs. The electrical circuit of the ball race may be overmolded by the electrically nonconductive ball race material such that the electrical circuit is spaced from the inwardly facing surface of the ball race. The distance by which the electrical circuit is spaced from the ball race is a distance which spans a normal amount of wear or rather the distance that generally corresponds to an amount of wear at which ball races typically fail. In essence, the distance between the inwardly facing surface and the electrical circuit is the distance at which the wear of the ball race becomes a safety concern.

The electrical circuit is connected to a sensor module that is connected to the ball stud by an electrical lead, wire or cable. In use the electrical circuit, the ball race, the sensor module, the electrical lead and the ball stud and ball head form a normally open circuit. With normal use of the ball joint, the layer of nonconductive material between the ball head and the electrical circuit of the ball race will wear away. When the ball head and the electrical circuit contact each other or rather when the ball race has worn to the extent that continued use may be dangerous, the open circuit will close such that energy can flow between the ball head and the electrical circuit. The sensor detects closing of the previously open circuit transmits a signal to an electronic control unit which in turn actuates at least one indicator to notify the driver that the ball joint needs to be serviced. The indicator can be in the form of a warning light that is illuminated when servicing of the ball joint is required. The indicator can also be an audible indicator which sounds intermittently until the ball joint is properly serviced.

In a standalone variation of the system for detecting overload, wear and/or failure of a ball joint, the sensor module itself comprises an indicator such as a button which, in a normal condition or operation of the ball race is positioned within the sensor module, but when the sensor module is actuated due to closure of the electrical circuit, the button pops out or projects out of the sensor module, thus providing a visual signal of ball joint failure. It is to be appreciated that instead of a button, the sensor module can comprise a different type of indicator such as a light source for example.

In accordance with yet another variation of the inventive system for detecting wear and/or failure of a ball joint, the ball race includes a ring having inwardly directed teeth. The ring is made from a material that squeaks/squeals when the teeth of the ring contacts and rubs against the steel outer surface of the ball head as the ball head moves within the ball housing with respect to the ball race. The teeth are sized such that the teeth are spaced at a distance from the inwardly facing surface of the ball race.

In a further variation the system for detecting overload, wear and/or failure of a ball joint, sensors that may be utilized in other drive systems of the automobile can be used to detect and identify high-load conditions on and/or misuse of the ball joint. When a high-load condition of the ball joint is detected, in the manner described above, the sensors will transmit signals to the electronic control unit which in turn transmits actuation signals to at least one indicator so as to notify the driver that the ball joint is under a high-load condition.

In yet another variation of the inventive system for detecting overload, wear and/or failure of a ball joint, the electrical circuit can be arranged on the ball race in such a location that the ingress of moisture into the ball joint or presence of moisture in the grease can be detected by a change in the resistance of the electrical circuit. The ingress of moisture into the ball joint can also be detected by means of a moisture or water sensor which can be located inside the ball joint.

It should be recognized that the ball race is generally the weakest structural component of a typical ball joint and as such, the load/force that is necessary to activate a sensor and transmit signals to the at least one indicator could be tuned to the specific automobile requirements based on specific control arm buckling/bending conditions for example. It is also possible that one variation of the inventive ball joint, the sensor can be integrated with other automobile control systems in which when a failure of the ball joint is detected, a "limp-home mode" of operation actuated. The limp-home mode of operation can include a specific manner of operating the transmission and/or engine of the automobile by means of the electrical control unit to ensure safe limited driving capability.

Yet another objective of the present invention is to provide a system and method for detecting overload, wear and/or failure of a ball joint. The system having a ball housing which retains a ball head of the ball joint therein. A ball race is received within the ball housing and receives the ball head of the ball joint. An inwardly facing surface of the ball race engages the ball head such that the ball head can pivot in relation to the ball housing. A detection component is supported by the ball race and is spaced from an exterior surface of the ball head by a set distance. The detection component issues an indicator signal to alert a driver when the detection component detects at least one of a worn or a failure condition of the ball joint.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. The invention will now be described, by way of example, with reference to the accompanying drawings in which.

It should be understood that the drawings are not necessarily to scale and that the disclosed embodiments are sometimes illustrated diagrammatically and in partial views. In certain instances, details which are not necessary for an understanding of this disclosure or which render other details difficult to perceive may have been omitted. It should be understood, of course, that this disclosure is not limited to the particular embodiments illustrated herein.

DETAILED DESCRIPTION OF THE PREFERRED EMBODIMENTS

The present invention will be understood by reference to the following detailed description, which should be read in conjunction with the appended drawings. It is to be appreciated that the following detailed description of various embodiments is by way of example only and is not meant to limit, in any way, the scope of the present invention.

Figure 1:
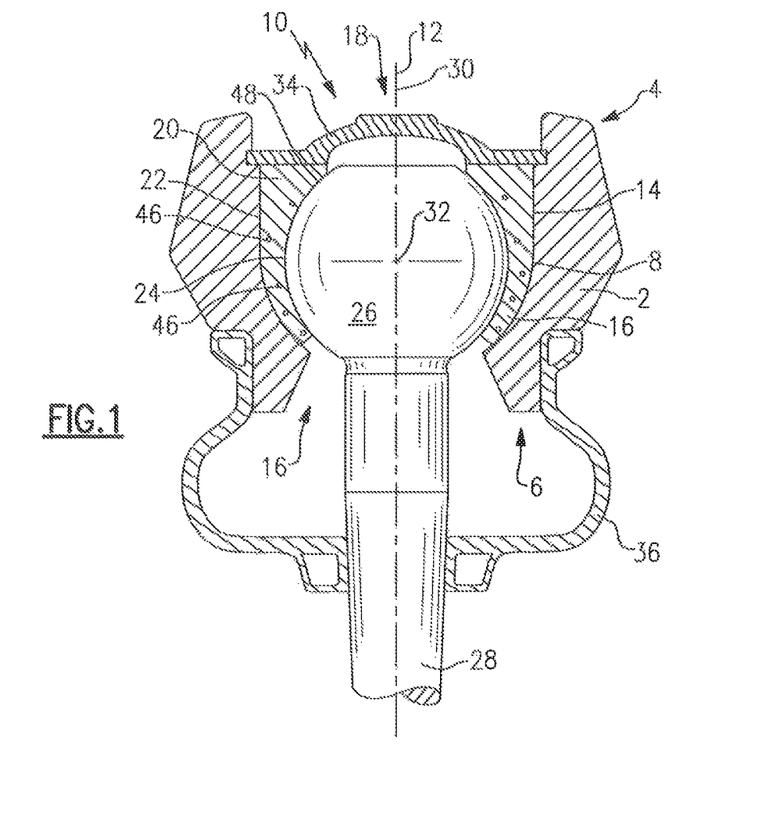
FIG. 1 is cross sectional view of a ball joint having a system for detecting overload, wear and/or failure of a ball joint.

Turning now to FIG. 1, the various components of a system for detecting wear and/or failure of a ball joint will now be brief described. The ball joint comprises a joint housing 2 that is open both at a top end 4 and a bottom end 6 thereof and an interior surface 8 that defines a passage 10 along a longitudinal axis 12. The interior surface 8 of the joint housing 2 has a top portion 14 that is generally cylindrical. A lower portion 16 of the interior surface 8 of the joint housing 2 slopes radially inward from the top portion 14 of the interior surface 8 to the bottom end 6 of the joint housing 2 in such a manner that the opening 16 at the bottom end 6 of the joint housing 2 has a diameter that is smaller than the diameter of the opening 18 at the top end 4 of the joint housing 2. A ball race 20 is received within the passage 10 of the joint housing 2 and has an exterior surface 22 with a profile that matches and/or mates with the interior surface 8 of the joint housing 2. An inwardly facing surface 24 of the ball race 20 has a contour that is generally spherical and is thus able to closely mate with the spherical ball head 26 of a ball stud 28 when the ball joint is in an assembled condition.

The ball head 26 may be composed of steel or other resilient metal, preferably the ball head 26 is made from a metal that is electrically conductive. The ball stud 28 extends axially from the ball head 26 through the opening 16 at the bottom end 6 of the joint housing 2. The ball stud 28 may be integral with the ball head 26 or, alternatively, the ball stud may be a separate component to which the ball head is rigidly fixed. For example, the ball head may have a threaded blind bore that accepts a threaded ball stud. The ball stud 28 is preferably made from a metal that is electrically conductive. In the assembled condition of the ball joint, the ball head 26 and thus the ball stud 28 are supported within the passage 10 of the joint housing 2 by the ball race 20 such that the ball stud 28 extends out through the opening 16 at the bottom end 6 of the joint housing 2. The spherical inwardly facing surface 24 of the ball race 20 retains the ball head 26 at fixed position along the longitudinal axis 12 defined by the passage 10 in the joint housing 2. That is to say, when assembled the ball head 26 and the ball stud 28 are generally axially fixed or rather prevented from moving along the longitudinal axis 10 with respect to the joint housing 2. However, due to the correspondingly, spherically shaped inwardly facing surface 24 of the ball race 20, the ball head 26 and the ball stud 28 to are able to rotate about a rotational axis 30 that is defined by the ball stud 28 and are able to pivot about a center point 32 of the ball head 26 in relation the joint housing 2.

A cap or rather a cover plate 34 may be fitted in an annular groove in the joint housing 2 over the ball head 26 and ball race 20. The cap 34 may effectively hold the ball head 26 and the ball race 20 in place within the joint housing 2. Alternatively, the joint housing 2 may be formed from a single piece such that ball head 26 and ball race 20 can be fitted in one side of housing before the joint is closed from the opposite side. Thus, in that alternative, a cap 34 may not be necessary.

The ball joint may include rubber sealing bellows 36. One end of the sealing bellows 36 is fixed to the bottom end 6 of the joint housing 2 while the opposite end of the sealing bellows 36 is secured to the ball stud 28. The sealing bellows 36 forms a seal around the joint housing 2 and the ball stud 28 and prevents dirt, moisture, or other contaminants from entering the passage 10 through the bottom end 6 of the joint housing 2. Dirt, moisture, and other contaminants are known to cause corrosion of the ball head 26 and increase the speed of wear in the ball joint and therefore reduce performance and the effective lifetime of the ball joint. The sealing bellows 36 is rubber or some other flexible material that resists dirt, moisture, or other contaminants.

Figure 12:
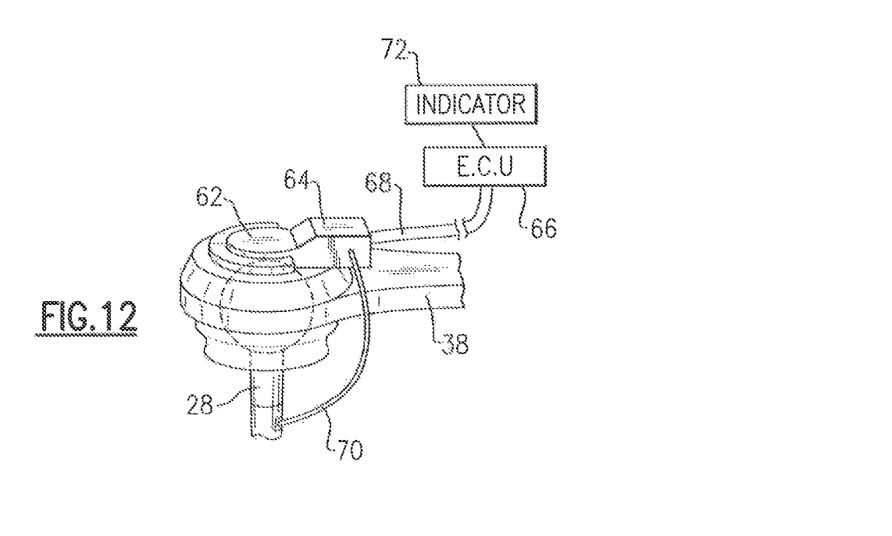
FIG. 12 is a diagrammatic view of a ball joint having a system for detecting wear and/or failure of a ball joint.
Figure 13:
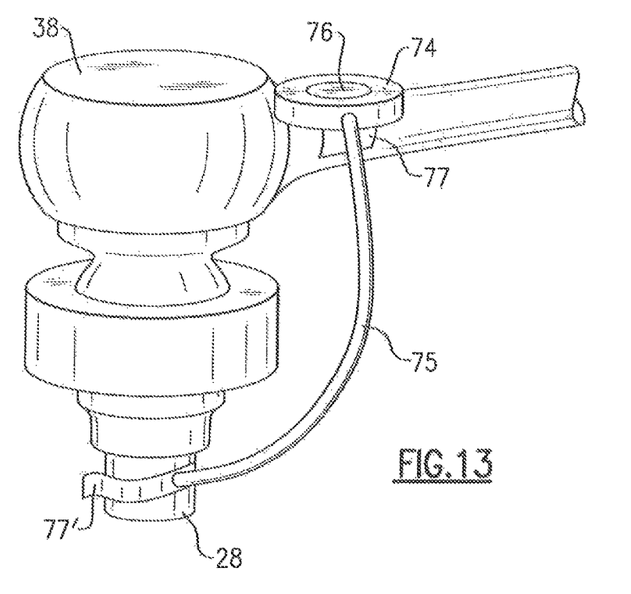
FIG. 13 is a diagrammatic view of a ball joint having a system for detecting wear and/or failure of a ball joint.

The ball joint may be installed, for example, in a vehicle's steering and suspension system such as a control arm linkage 38 (see FIGS. 12, 13). During operation of the vehicle, i.e., when the vehicle is being driven along a road, the ball joint enables two components in the steering and suspension system to move with respect to one another.

The ball race 20 may comprise a body 40 that has a slotted design to more easily fit over the ball head 26 upon installation/assembly. The body 40 may be in the form of petals or sections 42, 42' that allow the ball race 20 to spread open during installation/assembly, and then close again when installation of ball race 20 is complete. The body 40 of the ball race 20 is formed from a semi-rigid or resilient material such as acetal and Polyoxymethylene (POM) for example. Although a number of materials can be used to for the ball race 20. In the present invention it is beneficial that ball race 20 be made from an electrically non-conductive material. Lubricants such as grease, graphite, or oil may be used to lubricate the interface between ball head 26 and ball race 20.

In accordance with a first variation of the inventive system for detecting wear and/or failure of a ball joint, a framework 44 is located within the ball race 20, that is say the framework 44 is encased within the body 40 of the ball race 20 such as by means of an overmolding or fitting process. The framework 44 comprises a number of ribs or branches 46 that extend within the ball race 20 so as to substantially surround the ball head 26 in the area which the failure would be best detected. The ribs or branches 46 are formed from a material that is different from the material that forms the body 40 of the ball race 20. In this variation of the system for detecting wear and/or failure of a ball joint, the framework 44 can be located either partially or wholly within the body 40 of the ball race 20 or can be supported on the exterior surface 22 of the ball race 20. According to the invention the material that forms the framework 44 is generally harder or more resilient than the material that forms the body 40 of the ball race 20. Due to the difference in hardness/resiliency between the material of the body 40 and the material of the framework 44, when a sufficient force is placed on the ball joint for example when the vehicle hits a pot hole, curb or other obstruction or when the vehicle travels along a rough road at a high rate of speed, the ball race 20 can be deformed or otherwise damaged. The deformation of the framework 44 of the ball race 20 causes an uneven distribution of contact between inwardly facing surface 24 of the ball race 20 and the outside surface 48 of the ball head 26 as the ball stud 28 rotates, pivots, or moves withing the ball race 20 in relation to the joint housing 2. The uneven distribution of contact between the ball head 26 and the deformed ball race 20 results in audible noises that are noticeable by the driver of the vehicle. Since the framework 44 is located within the body 40 of the ball race 20 at a distance from the inwardly facing surface 24 thereof, when the material of the body 40 sufficiently wears away over time, the framework 44 will contact the outside surface 48 of the ball head 26. The distance by which the framework 44 is spaced from the inwardly facing surface 24 of the ball race 22 is described in more detail below with reference to an alternative to the framework 44. Contact between the framework 44 and the ball head 26 also results in audible noises that are noticeable by the driver of the vehicle. Continued driving of the vehicle can cause these noises to become louder. These noises inform or notify the driver of the automobile that the ball race 20, i.e., the ball joint has failed and, at the same time, signal that service of the automobile is required. Although the ball race 20 may be deformed thereby reducing operation of the ball joint, it is to be appreciated that the ball joint may still be functional for a limited amount of time, especially if the ball race 20 retains the ball head 26 in position within the ball housing 2.

Figure 2:
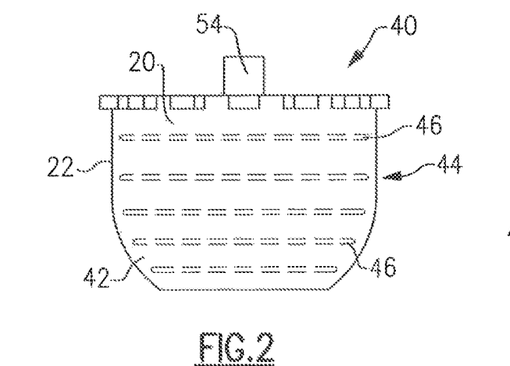
FIG. 2 is a view of a ball race of a ball joint comprising the system in accordance with FIG. 1.
Figure 3:
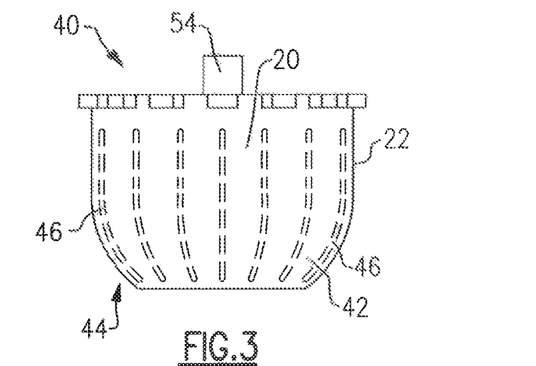
FIG. 3 is a view of a ball race of a ball joint comprising a variation of the system in accordance with the invention.

The framework 44 of ribs or branches 46 may be arranged in any manner that corresponds to the design of the body 40 of the ball race 20, but it should be understood that the framework 44 at least partially extends around a circumference of the ball head 26. FIG. 1 illustrates a cross sectional view of a ball joint that includes a framework 44 of ribs 46 that are generally horizontally aligned within the ball race 20 about the ball head 26. The horizontal arrangement of the ribs 46 can be seen in FIG. 2 in which the ribs 46 are shown as dashed lines that are arranged so as to be perpendicular with respect to the longitudinal axis 12 of the ball housing 2. FIG. 3 show a variation in which the ribs 46 are arranged vertically within the body 40 of the ball race 20. It is to be appreciated that the ribs 46 can be connected to each other and arranged in any orientation with respect to each other, for example the ribs 46 can crisscross, however it is important for the ribs 46 to extend around a majority of the perimeter of the ball head 26. It is also important to note that the ribs 46 can extend over a majority of the vertical height of the ball head 26.

Turning now to FIGS. 4, 5, and 7-12, a second variation of the present invention will now be described. As this embodiment is very similar to the previously discussed embodiment, only the differences between this new embodiment and the previous embodiment will be discussed in detail while identical elements will be given identical reference numerals.

Figure 5:
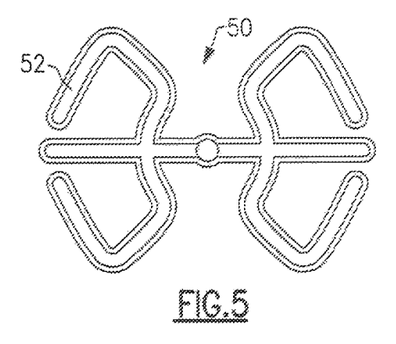
FIG. 5 is a diagrammatic layout of an electrical circuit of the system in accordance with FIG. 4.

In the second variation of the inventive system for detecting wear and/or failure of a ball joint, the ball head 26 is preferably formed from an electrically conductive metal such as steel, for example. The body 40 of the ball race 20 on the other hand is formed of a semi-rigid, resilient material that is electrically nonconductive. As shown in the figures, the body 40 of the ball race 20 comprises an electrical circuit 50 that is encased within the nonconductive material of the body 40 of the ball race 20 such as by means of an overmolding process. The electrical circuit 50 can be formed, for example, by a printed circuit or electrical leads that extend through the body 40 as ribs or branches 52. A two-dimensional layout of the electrical circuit 50 is shown in FIG. 5. To encase the electrical circuit 50 within the body 40 of the ball race 20, the electrical circuit 50 can be applied, i.e., printed or taped to an inner surface of a ball race 20 preform. After the electrical circuit 50 has been fixed to the preform body of the ball race 20, the ball race 20 may then be overmolded, for example, with the electrically nonconductive material.

Figure 6:
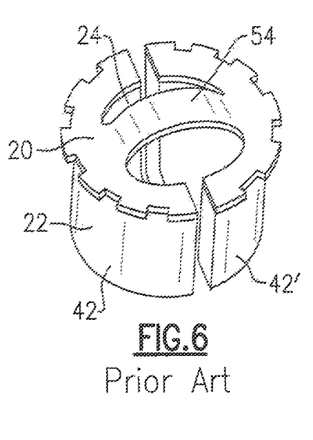
FIG. 6 is a perspective view of a standard ball race.
Figure 7:
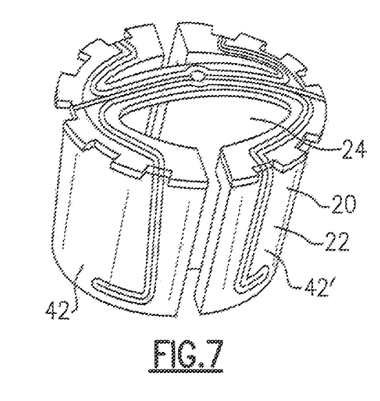
FIG. 7 is a perspective view of a ball race comprising an electrical circuit of the system in accordance with FIG. 4.
Figure 11:
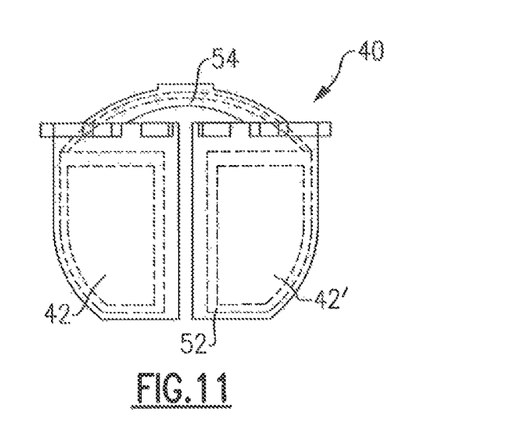
FIG. 11 is another plan view of a ball race comprising an electrical circuit of the system in accordance with FIG. 4.

The ribs or branches 52 of the electrical circuit 50 can have the layout as shown in FIG. 5 or the ribs or branches 52 of the electrical circuit 50 can extend within the body of the ball race 20 generally in any configuration so long as the ribs or branches 52 extend around the perimeter of the ball head 26 and along the vertical height of the ball head 26 to cover the main area related to wear and safety of the ball joint. FIG. 6 illustrates a standard ball race whereas the ball race 20 as shown in FIG. 7 comprises an electrical circuit 50 that extends generally around the perimeter of each of the petals or sections 42, 42' of the body 40 of the ball race 20. The layout of the electrical circuit 50 within the ball race 20 is diagrammatically shown as dashed lines in FIGS. 9-11. The electrical circuit of each of the petals or section 42, 42' are connected to each other via a bridge member 54 as shown in FIG. 11.

Figure 8:
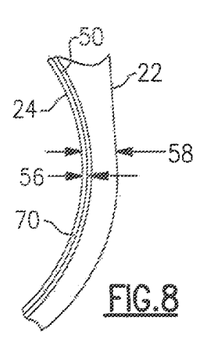
FIG. 8 is a sectional view of a portion of a ball race of the system in accordance with the invention.
Figure 9:
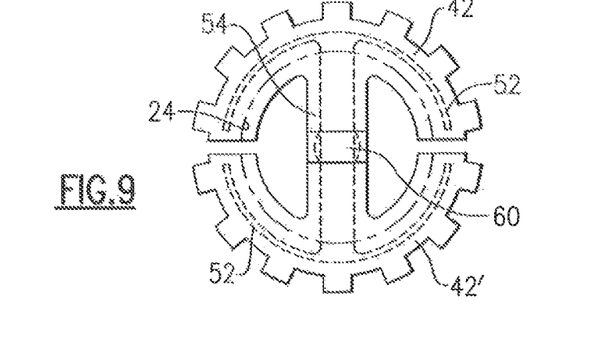
FIG. 9 is a top view of a ball race comprising an electrical circuit of the system in accordance with FIG. 4.
Figure 10:
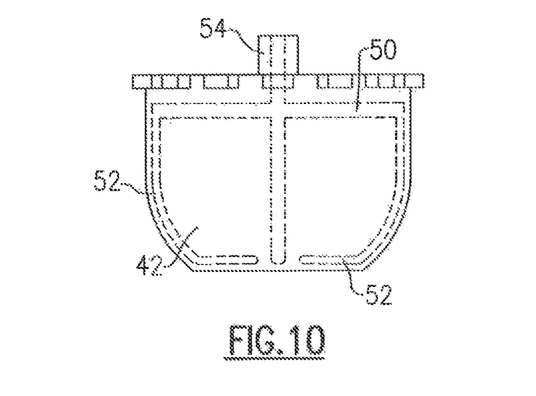
FIG. 10 is a plan view of a ball race comprising an electrical circuit of the system in accordance with FIG. 4.

Due to the overmolding process, the electrical circuit 50 is located within the body of the ball race 20 at a distance 56 from the inwardly facing surface 24 thereof. As such, the electrical circuit 50 is spaced from the electrically conductive outside surface 48 of the ball head 26. Particularly the electrical circuit 50 should be spaced from the inwardly facing surface 24 of the ball race 20 such that when the electrically conductive ball head 26 is received within the ball race 20, electrical energy cannot flow between the ball head 26 and the electrical circuit 50 in the ball race 20. As best shown in FIG. 8 the electrical circuit 50 is arrange so as to be closer to the inwardly facing surface 24 of the ball race 20 than the exterior surface 22 of the ball race 20. The petals or sections 42, 42' of the ball race 20 generally have a thickness 58 within a range of 1.0 mm to 2.0 mm, for example, the thickness 58 of the petals or sections 42, 42' of the ball race 20 may be 1.5 mm. The electrical circuit 50 is spaced from the inwardly facing surface 24 of the ball race 20 by a distance 56 of approximately between 0.2 mm and 0.8 mm, for example, the electrical circuit is spaced from the inwardly facing surface 24 of the ball race 20 by a distance 56 of approximately 0.5 mm. The distance 56 by which the electrical circuit 50 is spaced from the inwardly facing surface 24 of the ball race 20 is at least approximately a distance which represents a normal amount of wear or which rather generally corresponds to the amount of wear at which a ball race typically fails. In essence, the distance 56 between the inwardly facing surface 24 of the ball race 20 and the electrical circuit 50 is the distance at which wear of the ball race 20 becomes a safety concern.

The ball race 20 has a connection point 60 located generally centrally along the bridge member 54 between the petals or sections 42, 42' at which the electrical circuit 50 is exposed and can be coupled, via an electrical connector 62, to a sensor module 64. The sensor module 64 is in turn connected to an electrical control unit 66 by an electrical lead, wire or cable 68. The sensor module 66 can also be connected to the ball stud 28 by way of by another electrical lead, wire or cable 70.

Figure 14:
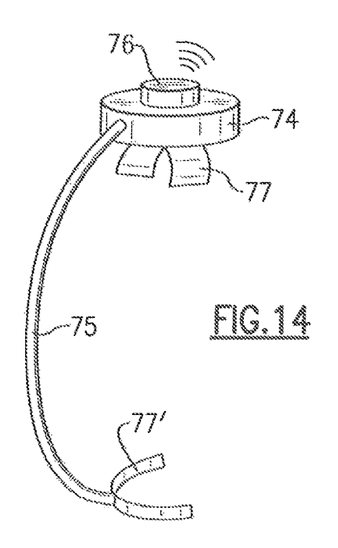
FIG. 14 is a diagrammatic view of the system in accordance with FIG. 13.
Figure 15:
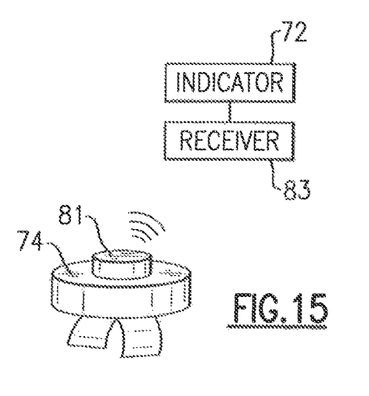
FIG. 15 is a diagrammatic view of a variation of the system in accordance with FIG. 13.

As the electrical circuit 50 is encased within the nonconductive material of the ball race 20 at a distance away from the ball head 26, the electrical circuit 50 is normally open. That is to say electrical energy does not pass between the ball head 26 and the electrical circuit 50 in the ball race 20 due to the layer 70 of nonconductive material that was overmolded onto the body 40 of the ball race 20. Over the operational life of the ball joint, the layer 70 of nonconductive material of the ball race 20 between the ball head 26 and the electrical circuit 50 will wear away. When the ball head 26 and the electrical circuit 50 come close enough or contact each other, electrical energy will be able to flow between the ball head 26 and the electrical circuit 50 in the ball race 20. The sensor module 64 detects the flow of electrical energy when the previously open circuit closes. When the circuit closes, the sensor module 64 transmits a sensor signal to the electronic control unit 66 which in turn transmits an actuation signal to at least one indicator 72 to notify the driver that the ball joint needs to be serviced. The indicator 72 can be a warning light which illuminates, or an audible indicator which produces an audible tone to inform the driver that servicing of the ball joint required In a standalone variation of the system for detecting wear and/failure of a ball joint as shown in FIGS. 13-15, the ball joint can comprise a self-contained system in which a sensor module 74 itself comprises an indicator 76. The sensor module 74 can include a clip 77 which is coupled to the control arm linkage 38. An electrical wire or lead 75 is coupled to the ball stud 28 by means of another clip 77'. The module 74 has an indicator button 76 which, under a normal condition of the ball race 20, is retracted within the sensor module 74 (FIG. 13), but when the sensor module 74 is actuated by detecting the flow of electrical energy, the button 76 pops out and/or projects out of the sensor module 74 (FIG. 14). It is to be appreciated that instead of a button, the sensor module 74 can comprise a different type of indicator 76 such as a light source that illuminates when actuated. In another variation of the system shown in FIG. 15, the sensor device 74 can comprise a transmitter 81 which wirelessly transmits an actuation signal to a receiver 83 that communicates with an indicator 72.

Figure 4:
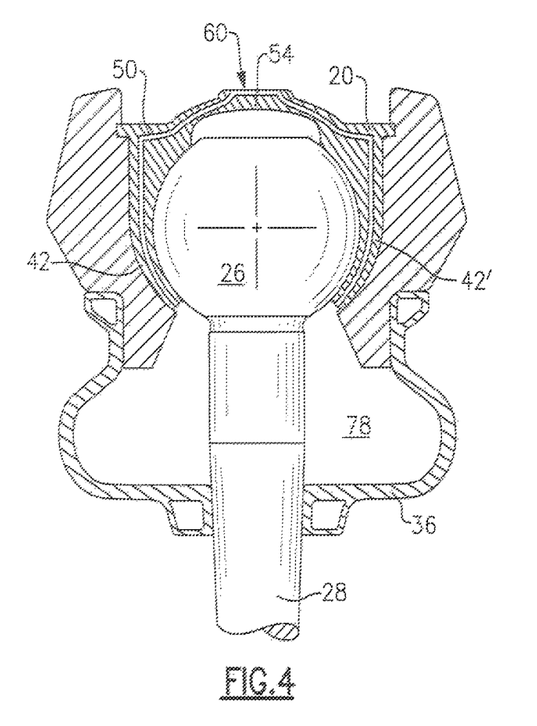
FIG. 4 is a cross sectional view of a ball race comprising a variation of the system for detecting overloading, wear and/or failure of a ball joint.

In a further variation of the inventive system for detecting wear and/failure of a ball joint, the electrical circuit 50 can be arranged on the ball race 20 in such a location that the ingress of moisture into the ball joint or the presence of moisture in the ball joint lubricant can be detected by the change of resistance in the electrical circuit 50. For example the electrical circuit 50 can extend to the lower end of the ball race 20 so as to be exposed to an open interior area 78 within the sealing bellows 36 (FIG. 4). The ingress of moisture into the ball joint can also be detected by means of a moisture or water sensor which can be located inside the ball joint. In this case, it is preferable to lubricate and protect the ball joint using a conductive grease.

Figure 16:
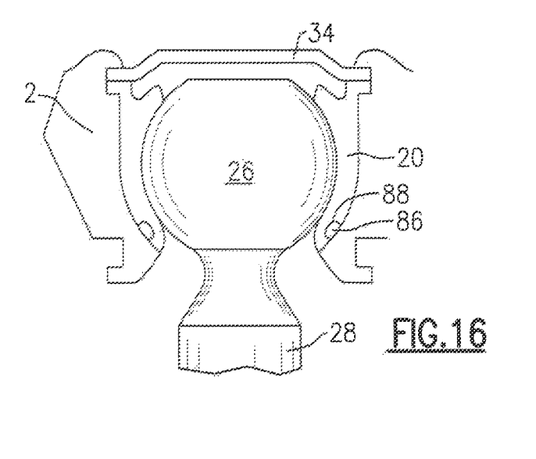
FIG. 16 is a diagrammatic view of a ball joint having a system for detecting wear and/or failure of a ball joint.
Figure 17:
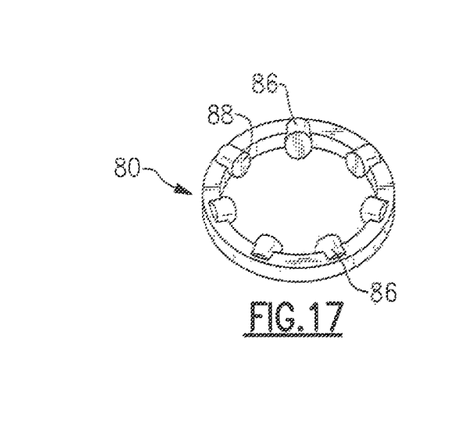
FIG. 17 is a diagrammatic view of a ring of the system in accordance with FIG. 16.

In accordance with yet another variation of the inventive system for detecting wear and/or failure of a ball joint, a ring 80, as shown in FIGS. 16 and 17, is located within the ball race 20 and is arranged along a lower portion 82 of the ball race 20 and radially surrounds a lower portion 84 of the ball head 26. The ring 80 is made from a material that is different from the material that forms the body 40 of the ball race 20. Preferably the ring 80 is made from a material that squeaks/squeals or otherwise produces sound when the ring 80 contacts and rubs against the steel outer surface 48 of the ball head 26 as the ball head 26 moves within the ball housing 2 with respect to the ball race 20. Preferably the ring 80 is made from ceramic, plastic or rubber material for example. In this variation, the ring 80 is embedded in an annular groove or channel in the exterior surface 22 of the ball race 20. The ring 80 comprises a number of teeth 86 that extend radially inward toward the ball head 26. The teeth 86 have inwardly directed faces 88 and are sized such that the faces 88 of the teeth 86 are spaced at a distance from the inwardly facing surface 24 of the ball race 20 and thus the outer surface 48 of the ball head 26 when the ring 80 is united with the ball race 20.

Figure 18:
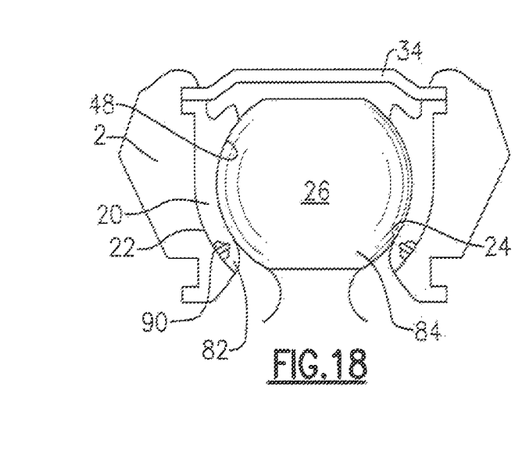
FIG. 18 is a diagrammatic view of a ball joint having a system for detecting wear and/or failure of a ball joint.
Figure 19:
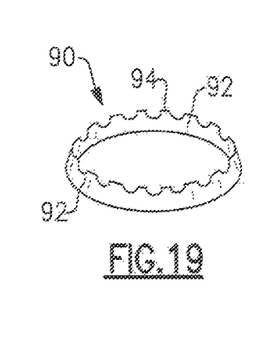
FIG. 19 is a diagrammatic view of a ring of the system in accordance with FIG. 18.
Figure 20:
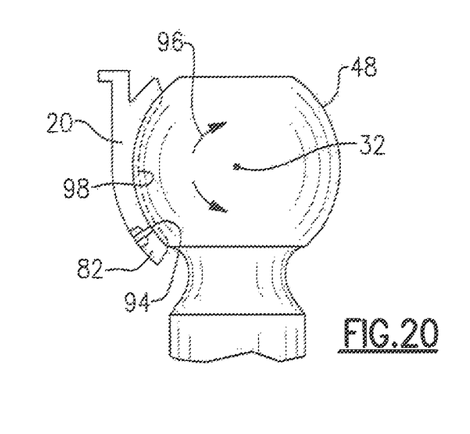
FIG. 20 is a diagrammatic view of the ball joint having the system in accordance with FIG. 18 with a ball race shown in a worn condition.

The ring can also be formed as a thin metal ring 90. In a particularly simple manner, thin metal rings 90 can be stamped from sheet metal and pressed to have the desired contour. FIGS. 18-20 illustrate a ball race 20 having a thin metal ring 90. Similar to the above described ring, the thin metal ring 90 has a number of teeth 92 that extend radially inward toward the ball head 26. The teeth 92 have inner surfaces 94 that are spaced at a distance from the inwardly facing surface 24 of the ball race 20 and thus spaced from the outer surface 48 of the ball head 26 when the thin metal ring 90 is united with the ball race 20. When the ball race 20 wears and the grease also degrades, the thin metal ring 90 comes into contact with the outer surface 48 of the ball head 26. In this condition when the ball head 20 oscillates, for example due to bumps on the road, as shown by arrows 96 in FIG. 20 the thin metal ring 90 will vibrate against the ball head 26 and/or the ball housing 2 thereby producing perceptible noise. It is to be understood that the above discussed toothed rings 80, 90 are merely examples as rings may be formed according to a variety of different shapes and/or contact patterns. The ball races 20 illustrated in FIGS. 16 and 18 are considered to be in a good working condition, that is to say the rings 80, 90 are spaced at a distance from the inwardly facing surface 24 of the ball race 20. In contrast, FIG. 20 illustrates a ball race 20 in a worn condition that needs to be replaced for proper functioning of the ball joint. In this figure, the teeth 92 of the ring 90 are in contact with the outer surface 48 of the ball head 26. Illustrated as a dashed line 98 in FIG. 20 is the inwardly facing surface 24 of the ball race 20 when the ball race 20 is in a new unworn condition. When the ball race 20 is in a new condition, as illustrated in FIG. 8, the teeth 88, 92 of the rings 80, 90 are spaced from the inwardly facing surface 24 of the ball race 20 by a distance 56 of approximately between 0.2 mm and 0.8 mm, for example, the teeth 88, 92 are spaced from the inwardly facing surface 24 of the ball race 20 by a distance 56 of approximately 0.5 mm. This distance 56 is at least approximately a distance which represents a normal amount of wear or which rather generally corresponds to the amount of wear at which a ball race typically requires replacement. The noises caused by contact between the teeth of the rings and the outer surface of the ball head inform or notify the driver of the automobile that the ball joint requires service, i.e., the ball race needs to be replaced.

In another variation of the inventive system for detecting wear and/or failure of a ball joint, sensors that are utilized in other drive systems, e.g., transmission control system of the automobile can be used to detect and identify high-load conditions on and/or misuse of the ball joint. When a high-load condition of the ball joint is detected, in the manner described above, the sensors will transmit signals to the electronic control unit which in turn transmits actuation signals to at least one indicator so as to notify the driver that the ball joint is under a high-load condition.

In accordance with a method for detecting overloading, wear, and/or failure of a ball joint, these conditions are detected by means of the following steps. Initially a ball joint is provided with a ball race having a detection component as described above. Following installation, the ball joint is allowed to function in a manner for with the ball joint was designed. During use of the ball joint, the inwardly facing surface of the ball race is allowed to wear such that a distance between a detection component of the system in the ball race and the outer surface of the ball head decreases. The detection component is then allowed to contact the outer surface of the ball head when the ball race is sufficiently worn. The system according to the invention then issues an indicator signal which is detectable to a driver of the vehicle. The system is designed and sized such when the indicator signal is issued, it is understood that the ball joint is in need of service.

While various embodiments of the present invention have been described in detail, it is apparent that various modifications and alterations of those embodiments will occur to and be readily apparent to those skilled in the art. However, it is to be expressly understood that such modifications and alterations are within the scope and spirit of the present invention, as set forth in the appended claims. Further, the invention described herein is capable of other embodiments and of being practiced or of being carried out in various other related ways. In addition, it is to be understood that the phraseology and terminology used herein is for the purpose of description and should not be regarded as limiting. The use of "including," "comprising," or "having," and variations thereof herein, is meant to encompass the items listed thereafter and equivalents thereof as well as additional items while only the terms "consisting of" and "consisting only of" are to be construed in a limitative sense.

We claim:

1. A system for detecting at least one of possible failure or sufficient wear of a ball joint, the system comprising:
    a ball housing;
    a ball race being received within the ball housing;
    a ball head being integrally fixed to an end of a ball stud, and the ball stud defining an axis;
    the ball head of the ball stud being received and retained within the ball housing with the ball race separating the ball head from the ball housing, and an inwardly facing surface of the ball race engaging with the ball head so that the ball head is movable relative to the ball housing;
    a detection component being supported by the ball race such that the detection component is initially spaced at a desired distance away from the inwardly facing surface of the ball race, and the detection component continuously extending over a majority of either an axial height or a lateral width of the ball head; and
    upon either failure or sufficient wear of the ball race, the detection component generates an indicator signal alerting a driver indicating that servicing of the ball joint is required, and the indicator signal only being generated when the detection component engages with an exterior surface of the ball head and there is relative movement between the ball head and the detection component.

2. The system according to claim 1, wherein the detection component is at least one metallic component which, upon either failure or sufficient wear of the ball race, contacts the exterior surface of the ball head to generate the indicator signal alerting the driver that servicing of the ball joint is required when there is relative movement between the detection component and the ball head.

3. The system according to claim 2, wherein the ball race is formed from a different material than the metallic component which forms the detection component and the material forming the ball race is less resilient than the metal forming the detection component, and the metallic component being a ring arranged in an exterior surface of the ball race and having a plurality of teeth which extend from the ring radially inwardly toward the exterior surface of the ball head.

4. The system according to claim 3, wherein the detection component comprises a framework which has a plurality of ribs that are each supported, in an initially installed condition of the ball race, at a distance of between 0.2 mm to 0.8 mm away from the inwardly facing surface of the ball race, and the framework substantially surrounds a perimeter of the ball head.

5. The system according to claim 3, wherein the detection component generates at least one of an audible and a tactile indicator signal, when the detection component rubs against the exterior surface of the ball head during relative movement between the detection component and the ball head, which alerts the driver indicating that servicing of the ball joint is required.

6. The system according to claim 3, wherein the detection component comprises an annular ring that is supported by the ball race and spaced from the inwardly facing surface of the ball race, the annular ring surrounds a perimeter of the ball head, and the annular ring is arranged adjacent an end of the ball race having an opening through which the ball stud extends.

7. The system according to claim 6, wherein an exterior surface of the ball race has a channel which receives the annular ring such that inwardly facing surfaces of the annular ring are spaced, in an initially installed condition of the ball race, between 0.2 mm to 0.8 mm from the inwardly facing surface of the ball race.

8. The system according to claim 6, wherein the annular ring generates at least one of an audible and a tactile indicator signal which identifies, when the annular ring rubs against the exterior surface of the ball head, which alerts the driver indicating that servicing of the ball joint is required.

9. The system according to claim 2, wherein the detection component comprises a framework which has a plurality of ribs that are accommodated within the ball race and the plurality of ribs continuously extending circumferentially around an outer surface of the ball head over a majority of either the axial height or the lateral width of the ball head, and each one of the plurality of ribs, in an initially installed condition of the ball race, is spaced away from the inwardly facing surface of the ball race.

10. A system for detecting at least one of possible failure or sufficient wear of a ball joint, the system comprising:
    a ball housing having an interior surface;

a ball race having an inwardly facing surface and an exterior surface, the ball race being received within the ball housing such that the exterior surface of the ball race mates with the interior surface of ball housing, and the ball race being formed from a first material;

a ball stud having a ball head being integrally fixed to an end of the ball stud, and the ball stud defining an axis;

the ball head of the ball stud being received and retained within the ball housing with the ball race separating the ball head from the ball housing, and the inwardly facing surface of the ball race engaging with the ball head such that the ball head is movable relative to the ball race and the ball housing;

a detection component being supported by the ball race such that the detection component is initially spaced at a desired distance away from the inwardly facing surface of the ball race, the detection component be formed from a second material that is either relatively harder or more resilient than the first material that forms the ball race, and the detection component continuously extending over a majority of at least one of an axial height of the ball head and a lateral width of the ball head; and upon either failure or sufficient wear of the ball race, the detection component mechanically generating an indicator signal by contact between the detection component and the exterior surface of the ball head and movement of the ball head relative to the detection component, and the mechanically generated indicator signal alerting a driver indicating that servicing of the ball joint is required.

\* \* \* \* \*